(12) United States Patent
Stefanick

(10) Patent No.: US 6,277,443 B1
(45) Date of Patent: Aug. 21, 2001

(54) LOW LEAD OR NO LEAD BATCH GALVANIZATION PROCESS

(75) Inventor: Gary M. Stefanick, Hubbard, OH (US)

(73) Assignee: John Maneely Company, Wheatland, PA (US)

( * ) Notice: Subject to any disclaimer, the term of this patent is extended or adjusted under 35 U.S.C. 154(b) by 0 days.

(21) Appl. No.: 09/107,658

(22) Filed: Jun. 30, 1998

(51) Int. Cl.⁷ .............................. B05D 1/18; B05D 1/38; B05D 3/02

(52) U.S. Cl. ..................... 427/321; 427/234; 427/310; 427/329; 427/433; 427/436; 34/105; 34/107; 34/217

(58) Field of Search ................................. 427/310, 311, 427/321, 329, 433, 436, 234; 118/64, 74; 34/217, 236, 237, 104, 105, 107

(56) References Cited

U.S. PATENT DOCUMENTS

| | | | |
|---|---|---|---|
| 2,114,975 | * | 4/1938 | Camerota ........................... 427/234 |
| 2,481,130 | * | 9/1949 | Lindemuth ............................ 34/105 |
| 4,238,532 | * | 12/1980 | Dreulle ................................. 427/309 |
| 4,567,674 | * | 2/1986 | Strohmeyer, Jr. ..................... 34/57 A |
| 4,628,615 | * | 12/1986 | Verheyden ............................... 34/34 |
| 4,802,932 | * | 2/1989 | Billiet ................................... 148/23 |
| 4,859,276 | * | 8/1989 | John, Jr. et al. ..................... 156/626 |
| 5,437,738 | * | 8/1995 | Gerenrot et al. ..................... 148/26 |

OTHER PUBLICATIONS

Wheatland Tube Company Product Literature, Jan. 1998.
Wheatland Tube Company—Company Brochure. No Date Available.
"Process for Batch Hot Dip Galvanizing with Lead Free Zinc" by Dr. Yume Grot and Thomas L. Ranck, paper presented at American Galvanizing Association Seminar, Oct. 24, 1994, Detroit, Michigan.
Annual Book of ASTM Standards, B–6, p. 194, Table I, 1977.
Declaration of inventor., Oct. 28, 1998.

* cited by examiner

Primary Examiner—Shrive Beck
Assistant Examiner—Michael Barr
(74) Attorney, Agent, or Firm—Calfee, Halter & Griswold, LLP (57) ABSTRACT

A batch process for making galvanized steel products with a low lead or no lead zinc coating is described. Metal parts are cleaned, rinsed, pickled and rinsed and are immersed in a hot, pre-flux solution and thoroughly dried before they are immersed in a molten zinc bath. The dryer system includes a mechanism for rotating the batch of parts as they are dried. In one embodiment of the invention, a batch of steel pipe is dried by hot air having a maximum temperature of 125° C. The descrambler system rotates the pipe and moves the pipe in contact with the divider apparatus to separate the pipe in the dryer. The pipe, thoroughly dried, is immersed into a molten zinc bath having less than 0.05% by weight lead, and the use of a top-flux on the molten zinc bath is optional.

29 Claims, 6 Drawing Sheets

Fig. 6

LOW LEAD OR NO LEAD BATCH GALVANIZATION PROCESS

FIELD OF INVENTION

This invention relates generally to a batch process for making galvanized steel products with a low lead or no lead galvanized coating, and more specifically, to a galvanizing process in which metal parts are treated in an aqueous pre-flux solution and then thoroughly dried before they are immersed in a molten zinc bath that is low lead or no lead.

BACKGROUND

Galvanized coatings are commonly applied for corrosion protection of metal parts, and especially steel or iron parts. In the galvanizing process, a solidified layer of zinc is formed on a part's surfaces by immersing the part into molten zinc which contains approximately 1% lead. The main benefit of lead's presence in zinc is that it makes the process of galvanizing less demanding and less sensitive to many unfavorable circumstances, like insufficiently pickled, cleaned and even rusty steel surfaces, the absence of preheating and even drying when wet parts are immersed in molten zinc, and so on.

Unfortunately, lead cannot now be used for galvanizing steel parts coming into contact with drinking water, since small but significant quantities of lead from the galvanized parts dissolve in the water. Such dissolved lead may be accumulated in human and animal bodies with very deleterious results. Consequently, a number of state legislatures have passed laws which, since 1995, forbid the presence of lead in galvanized products which contact drinking water.

Attempts have been made to reduce the lead level from conventional levels, for example, containing a maximum of about 1.4% by weight lead in Prime Western grade zinc to a High Grade Standard requirement level of a maximum of about 0.03% by weight lead, or to a Special High Grade Standard requirement of a maximum of about 0.003% by weight lead (ASTM B6-87 standard). However, attempts to reduce lead to less than about 0.5% by weight of lead have resulted in insufficient wetting of steel parts and finished products having a high percentage of uncoated surfaces, that is, black or bare spots.

Other techniques have been developed in the galvanization process in conjunction with the use of lead to produce high quality galvanized coatings. Metal parts are usually treated with aqueous solutions prior to immersing the parts into the galvanizing bath. Metal parts typically undergo alkaline cleaning, rinsing, acidic pickling, and rinsing treatments. After the parts have been cleaned, rinsed, pickled and rinsed, they are usually immersed in a pre-flux solution which is an aqueous solution containing ammonium chloride or a mixture of ammonium chloride and zinc chloride. The application of pre-flux has been found to remove metal oxides, for example, iron oxide from steel part surfaces, to promote good wetting with the molten zinc.

A top flux is often employed in conventional processes. Top fluxes are typically comprised of the same ingredients as a pre-flux, except that the salts such as zinc chloride and ammonium chloride are molten in form and float on top of the galvanizing bath. Top fluxes have the further advantage that they reduce or eliminate metal spattering when steel articles are immersed into the galvanizing bath, which can occur if the article is still wet with aqueous solutions such as pre-flux.

As a metal part having a surface temperature substantially lower than the molten zinc is immersed in the molten zinc bath, a frozen layer of zinc is formed on the surface of the part. The frozen zinc layer forms before the molten zinc is able to adequately wet the surface of the steel, and hence there is poor adhesion of the frozen zinc onto the metal part surface. However, soon thereafter, the frozen layer on the part surface gradually melts. When the layer is totally melted, the metal surface is wetted by molten zinc and growth of a zinc-metal intermetallic alloy forms an integrated surface between the zinc and the metal part.

Perhaps the most significant benefit of lead is that it accelerates the melting of the frozen zinc layer on the surface of the part, and galvanization takes place more rapidly. This phenomenon is described in U.S. Pat. No. 5,437,738. Lead also significantly reduces surface tension of molten zinc and increases its fluidity. This results in better wetting of the steel surface to be coated and higher drainage after withdrawal of the parts from the kettle. Another technique that has been used to accelerate the rate of galvanization, is to preheat the parts after the parts are immersed in pre-flux. Preheating is typically conducted at high temperatures, for example, greater than 200° C., so that the steel surfaces are wetted by molten zinc as rapidly as possible. Also, parts that are arranged in a batch have many contact surfaces with adjacent parts and require additional heat for drying. Since conventional pre-fluxes are decomposed or burned when heated, for example, to 200° C. to 250° C. for 3 to 15 minutes, a non-conventional, heat-stable pre-flux is needed.

It is desirable to provide a new galvanizing process that is low-lead or no lead for producing uniform, void-free coatings on metal parts. It is desirable to provide a galvanization process that essentially thoroughly dries the parts after the parts are immersed in a conventional pre-flux solution. It is also desirable to provide a galvanization process in which the top-flux treatment can be eliminated. It is desirable that the galvanizing process can be carried out in batch operation. In addition, it is desirable to provide a low-lead or no-lead galvanizing process with galvanizing baths that may contain low concentrations of aluminum to promote adhesion and a bright finish to the galvanize coating.

SUMMARY OF THE INVENTION

The invention herein provides for a low-lead or no-lead batch galvanization process that produces void-free zinc coatings on metal parts. The molten zinc bath contains about 0.1% or less, preferably, about 0.05% or less, more preferably, about 0.005% or less, and even more preferably, about 0.003% or less by weight lead. Metal parts to be galvanized typically undergo one or more of the cleaning, rinsing, pickling, and pre-flux treatments in aqueous solutions, the aqueous solutions being well known in the art. According to the invention herein, the process comprises applying a pre-flux solution having a temperature of at least about 65° C.; drying the surface of the parts such that the surface of the parts are essentially dry, and the surface temperature of the parts is maintained at about 125° C. or less; and applying molten zinc to the parts to form a galvanized coating on the parts. The wet parts are dried, preferably, by placing them in a dryer system that passes hot, dry air over the surface of the parts while the parts are rotated.

In one embodiment of the invention, a plurality of steel pipe, arranged in a batch, are treated in a series of aqueous solutions. The pipe members are preferably washed, rinsed, and then dipped in pre-flux solution having a temperature of at least about 65° C. and comprising ammonium chloride in water. Next, the batch of pipe members are placed in a dryer system and each pipe is essentially, thoroughly dried such that the surfaces of the pipe achieve a maximum temperature of about 125° C. The pipe members in the batch, while in the dryer system, are rotated in a motion relative to one another by a rotating system during drying.

The rotating system preferably comprises a descrambler system and more preferably, both a descrambler system and a divider apparatus. The descrambler system rotates a batch of wet pipe to the dryer system that comprises a hot, dry air source. The pipe members are arranged such that the surface of each pipe is in contact with the surfaces of adjacent pipe. As the descrambler system rotates the batch of pipe within the dryer system, the individual pipe rotate along their longitudinal axes. The pipe rotate relative to one another, and as they rotate, their original contact surfaces become exposed to dry air when they establish new contact surfaces with adjacent pipe.

Even more preferably, as the descrambler system rotates the batch of pipe, the batch of pipe contacts the divider apparatus. When the batch of pipes contacts the divider apparatus, several pipe members become separated from adjacent pipe members, and also, pipe members that are situated in around the center of the batch, can be rotated to a greater degree relative to adjacent pipe. The descrambler system can cause the batch of pipes to come into contact with divider apparatus several times while the batch is exposed to dry air. When the descrambler system transports the batch of pipe out of the dryer system, the individual pipes are essentially, thoroughly dry.

The invention herein preheats the parts to a maximum temperature of about 125° C. and a temperature at which the pre-flux is stable for extended periods of time without decomposing or burning. Parts that have been immersed in conventional pre-flux solution can be retained in the dryer for extended periods of time with no detrimental effect because of the low temperature used for preheating during the process of this invention.

The invention herein also eliminates the need for a top flux. As metal parts enter the molten zinc bath, the spattering is essentially eliminated due to the thoroughness of drying. This invention also works with a top flux and the use of a top flux is optional.

DETAILED DESCRIPTION OF THE INVENTION

The present invention described herein provides for a batch galvanization process that produces continuous, defect-free zinc coatings on metal parts, and particularly iron or steel parts. Specifically, the invention herein provides for a batch galvanization process that is low-lead, or no lead and contains about 0.1 or less, preferably about 0.5% or less, more preferably about 0.005% or less, and even more preferably about 0.003% or less by weight lead. Metal parts that are to be galvanized typically undergo a combination of cleaning, rinsing, pickling, and pre-flux treatments in aqueous solutions, the aqueous solutions being well known in the art. According to the invention herein, the process comprises immersing metal parts in a pre-flux solution having a temperature of at least about 65° C.; drying the surface of the parts, such that the surfaces of the parts are essentially, thoroughly dried, their surface temperatures being no greater than about 125° C.; and applying molten zinc to the parts to form a galvanized coating on the parts. The wet parts are dried, preferably, by placing them in a dryer system that passes dry air over the surface of the parts while the parts are rotated. The dryer system comprises a system for rotating the parts as the parts are dried.

More specifically, metal parts to be galvanized are typically cleaned in an alkaline solution and rinsed in water. After cleaning, the parts are preferably pickled and rinsed in water, then treated in an aqueous pre-flux solution comprising ammonium chloride, zinc chloride or both. According to the inventive process herein, the parts are essentially, thoroughly dried in a dryer system that raises the surface temperature of the parts to a maximum temperature of about 125° C. The rate at which the parts can be thoroughly dried depends upon the volume flow, temperature and humidity of air. The dry rate is also dependent upon the geometry, size and number of parts in the batch that is retained in the dryer system.

Figure 1:
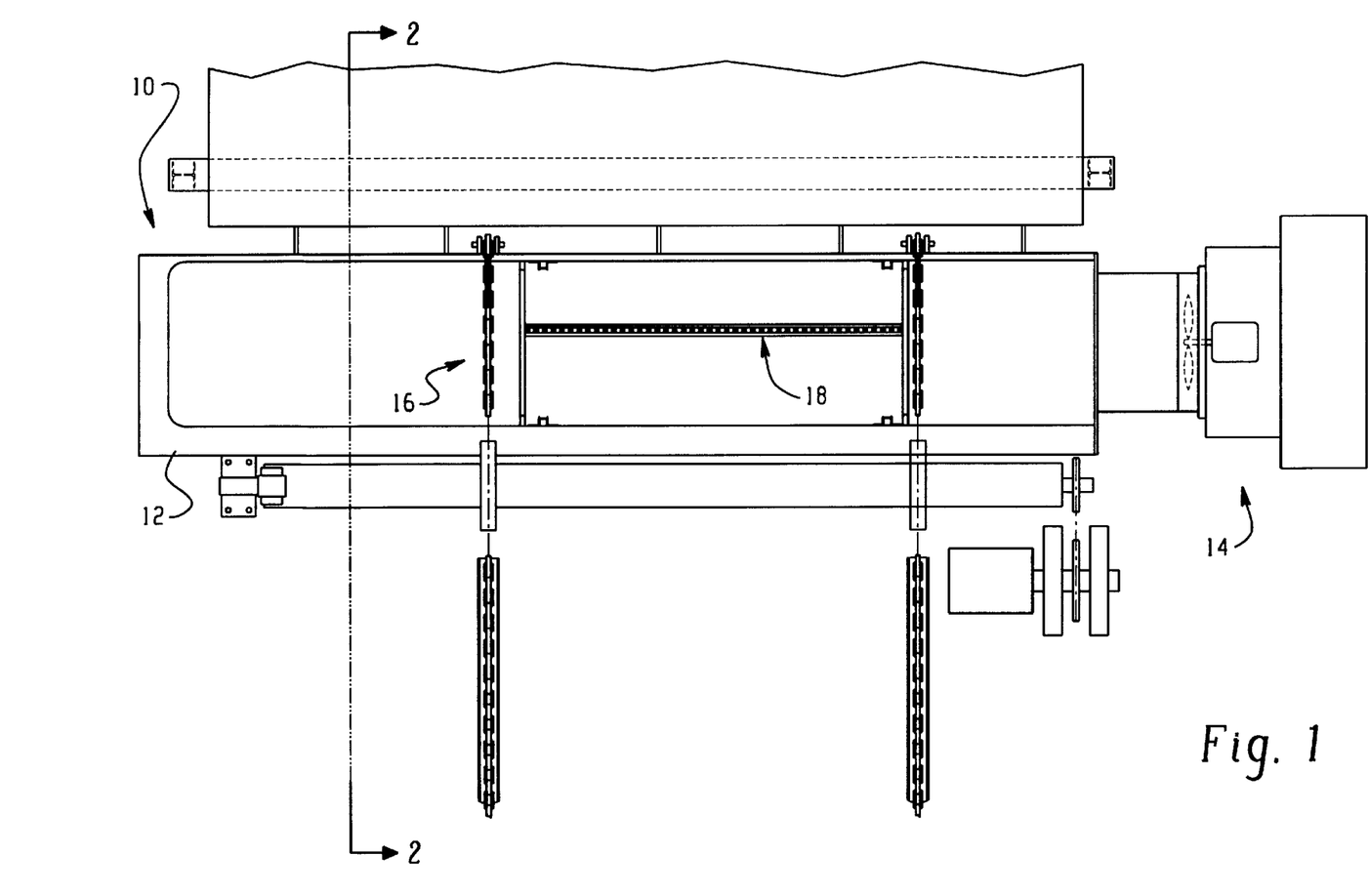
FIG. 1 is a top plan view of the dryer system that is used in a lead-free or near lead-free galvanizing process of the present invention.

FIG. 1 is a top plan view of dryer system 10 that is used in a low lead or no-lead galvanization process of the present invention. Dryer system 10 comprises a housing or tank 12 and dry air source 14, descrambler system 16, and preferably, divider apparatus 18. Dry air source 14 is preferably a hot air system that includes a blower and a plurality of steam coils. The blower pulls ambient room air through a filter and circulates the air through a series of steam coils that warm the air, to a maximum temperature of about 125° C.

Descrambler system 16 is a method for separating and rotating parts such that they can be exposed to the flow of hot, dry air that is blown from dry air source 14. Descrambler system 16, as it separates the metal parts, also rotates the metal parts preferably, such that all surfaces of the parts can be exposed to the dry air that is generated by dry air source 14.

The metal parts to be galvanized can be arranged in a batch comprising at least two parts that are in contact with one another at a contact surface. Dryer system 10 of the invention herein comprises a rotating system for rotating the individual parts relative to one another. The system for rotating individual parts comprises a descrambler system that can transport the parts, and in doing so, can rotate the parts relative to one another. An example of a descrambler system is shown as descrambler system 16 of FIG. 1.

Even more preferably, the rotating system for rotating metal parts relative to one another comprises both a descrambler system and a divider apparatus, such as, for example descrambler system 16 and divider apparatus 18 of FIG. 1. A descrambler system in conjunction with a divider apparatus is preferably used when the number of parts that are arranged in a batch is too large for adequate rotating motion relative to the size of the dryer system. In such circumstances, the divider apparatus provides contact interference with the parts transported by the descrambler system. Depending upon the total surface area of the parts of the batch to be dried, for example, if the parts are relatively large or relatively fewer in number, the movement of parts by the descrambler system can be adequate to rotate the parts for thorough drying. It is important that upon leaving dryer system 10, the individual parts are rotated so that all contact surfaces are adequately exposed to dry air and are essentially thoroughly dried.

Figure 2:
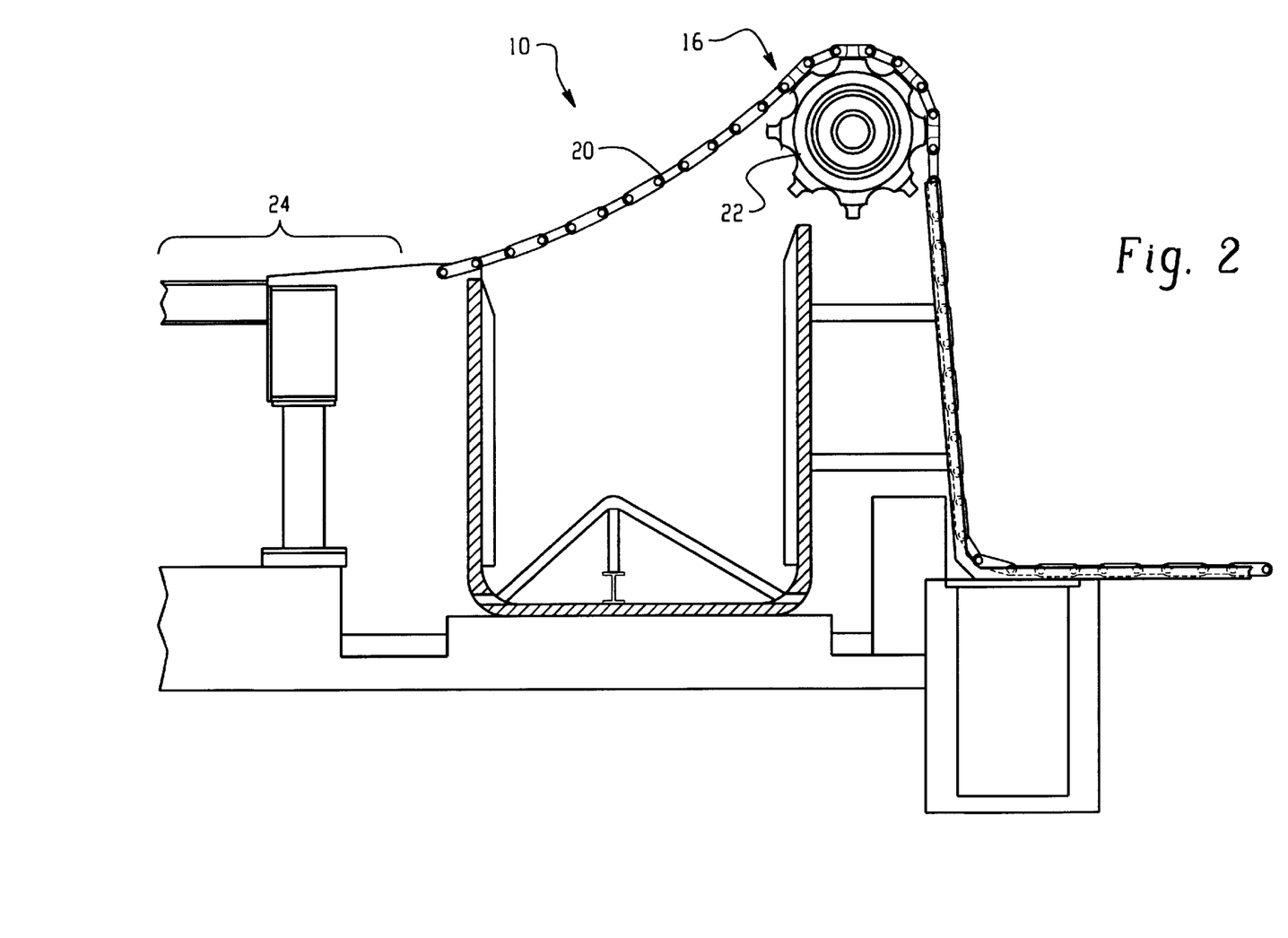
FIG. 2 is a sectional view of the dryer system taken substantially on the plane designated by the line 2—2 of FIG. 1 showing the empty chain of the descrambler system in the "up" position.

FIGS. 2 through 5 illustrate one embodiment of the inventive process herein. FIG. 2 illustrates a cross-sectional view of dryer system 10 that is used in the process of this invention. Descrambler system 16 preferably includes support chains 20 and sprocket 22 that operate together to rotate the metal parts within dryer system 10. Sprocket 22 can rotate to lift and lower chain 20. The asymmetric movement of chain 20 as it is pulled from one direction, causes parts to move relative to one another. In addition, descrambler system 16 preferably operates to transport and rotate metal parts out of dryer system 10 to galvanizing feeder station 24.

Figures 3, 3A:
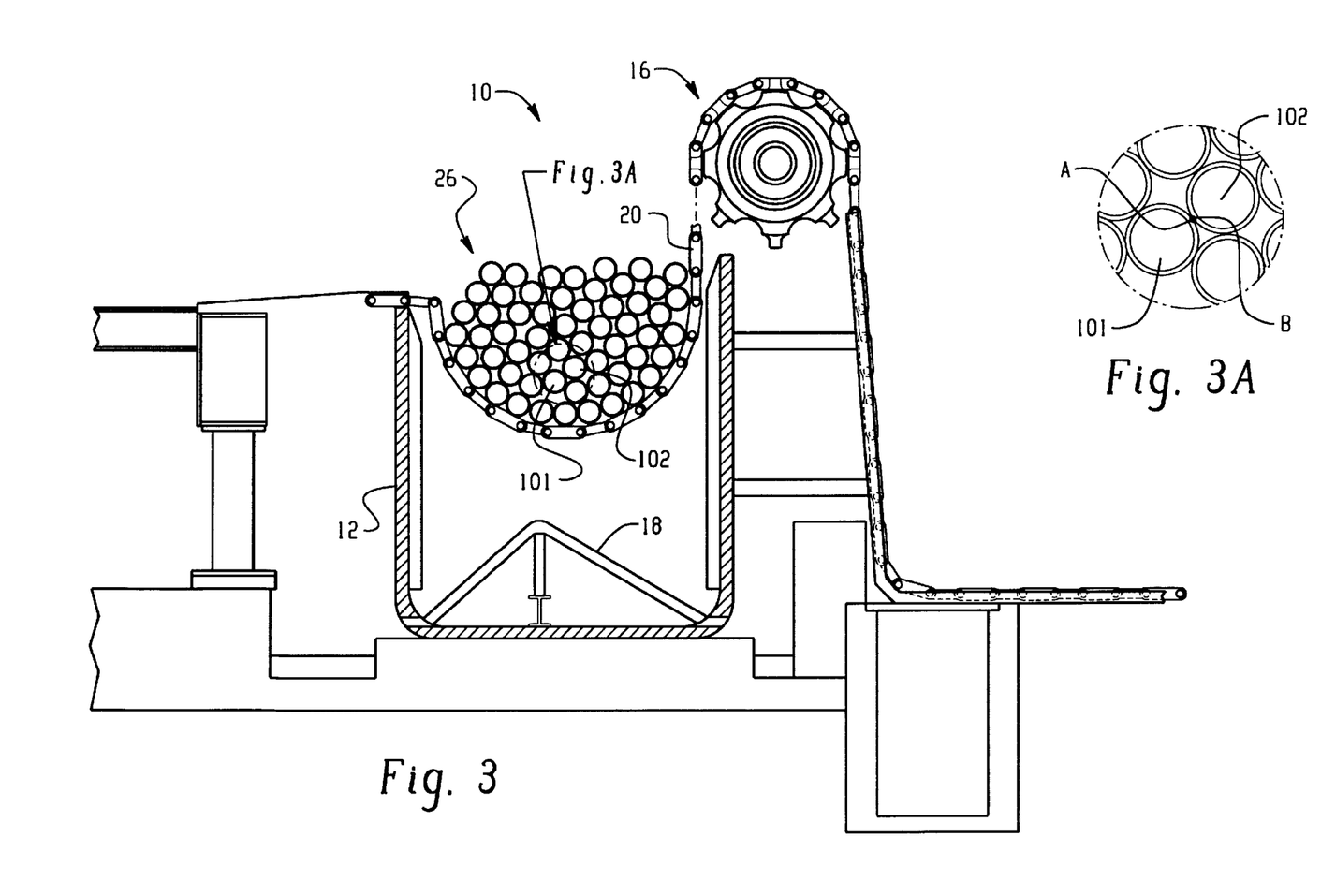
FIG. 3 is a view similar to FIG. 2 showing a batch of steel pipe that is being transported into the dryer system according to the galvanizing process of the present invention.
FIG. 3a is an enlarged view of the pipe shown in FIG. 3, and illustrates the contact surfaces between adjacent pipe.

FIG. 3 shows batch of pipe 26 being rotated by descrambler system 16 of dryer system 10. The pipes are arranged in a batch such that the surface of each pipe member is in contact with adjacent pipe substantially along the longitudinal surfaces of adjacent pipe. Dry air source 14 (not shown) is located adjacent to tank 12 such that the flow of air is substantially parallel to the longitudinal surfaces of the pipe. FIG. 3 shows batch of pipe 26 being lowered on support chains 20 of descrambler system 16 into tank 12 and within the path of dry air that is directed by dry air source 14.

FIG. 3a shows a more detailed view of the pipe arranged in a batch and the interstitial spaces of air flow. As the batch is being lowered, for example, member pipe 101 remains in contact with adjacent pipe member 102 at contact surfaces A and B, respectively. At these contact surfaces, pipe 101 and pipe 102 can remain wet with aqueous pre-flux solution until surfaces A and B rotate and come in contact with the dry air that flows through the interstitial spaces of the pipe. Pipe members within the batch can roll or slip and rotate in a radial direction to form new contact surfaces with adjacent pipe members without the batch having had contact interference by divider apparatus 18. However, if the surface area of the pipe in the batch is large, some of the pipe members in the batch can remain in contact with adjacent pipe members at fixed contact surfaces before the batch comes into contact with divider apparatus 18.

Figure 4:
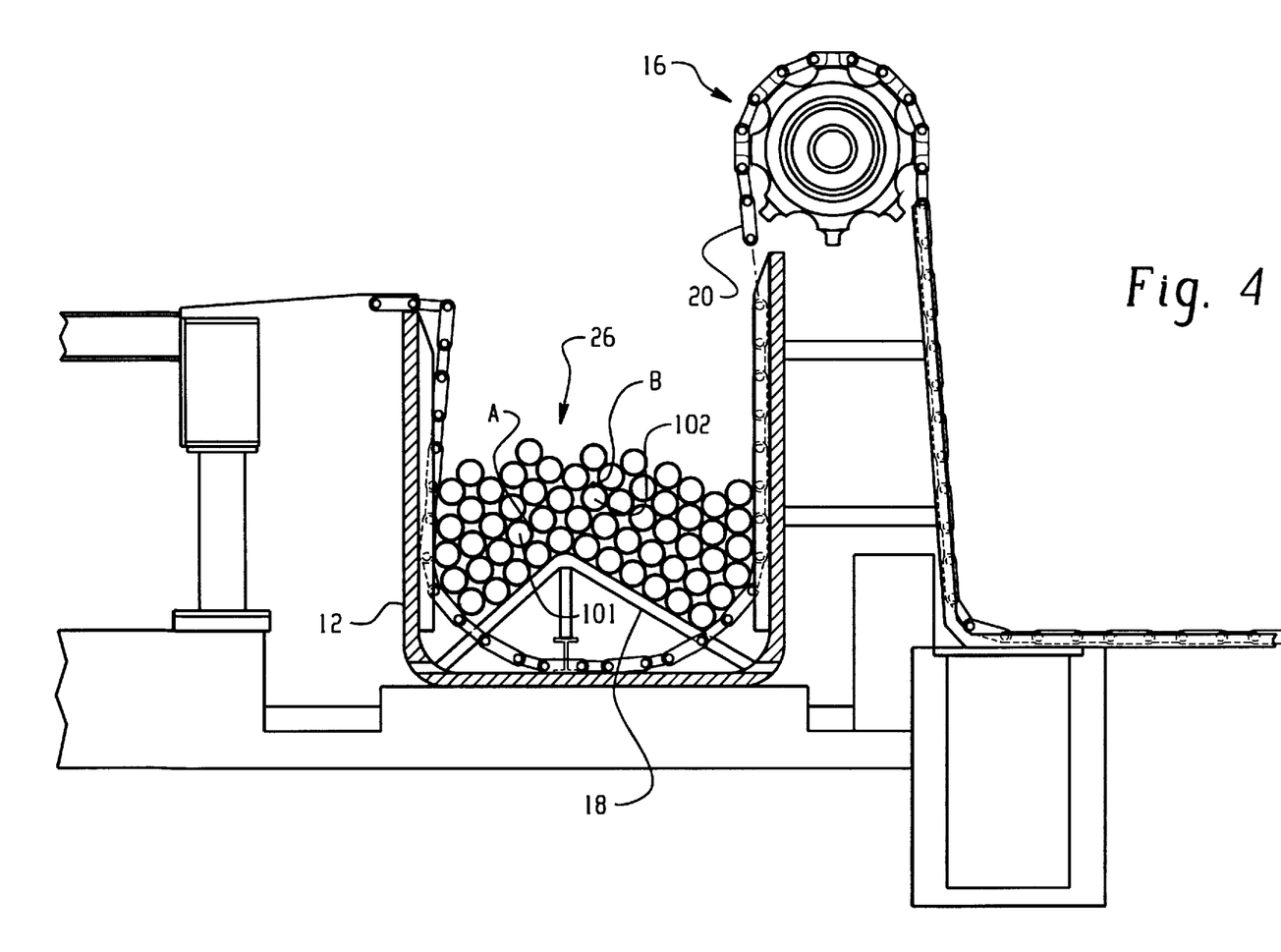
FIG. 4 is a view similar to FIG. 3, showing individual pipe members rotated about their axes after the pipe has been in contact with the divider apparatus and while being exposed to dry air.

When the batch of pipe members comes in contact with divider apparatus 18, FIG. 4 shows that the contact causes many of the pipe members to separate from adjacent pipe members. The contact of the batch with divider apparatus 18 also causes many or all of the pipes to rotate in a radial direction. For example, pipe member 101 and pipe member 102 are no longer in contact and with each other. It is also possible that pipe members 101 and 102 remain in contact with each other and that contact surface A is no longer in contact with contact surface B. If the batch of pipe comes in contact with the divider apparatus 18 only once, it is possible that several pipes of the batch remain in the original contact positions with adjacent pipe. Accordingly, it may be necessary that descrambler system 16 transports the batch of pipe in and out of contact with divider apparatus 18 two or more times to ensure that all of the pipe in the batch are essentially, thoroughly dried.

Figure 5:
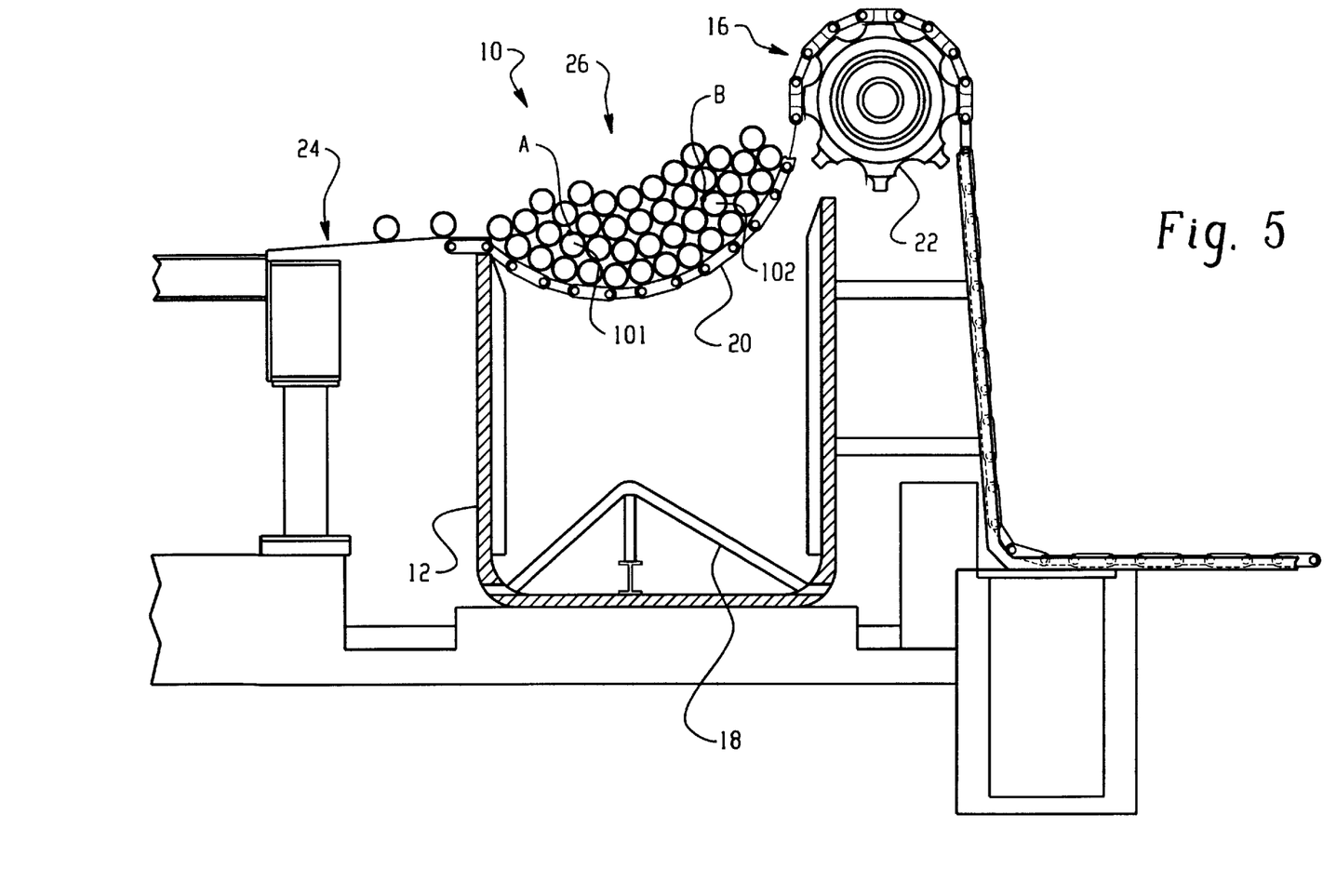
FIG. 5 is a view similar to FIG. 4, of the dryer system showing a batch of steel pipe being rotated out of the dryer system.

FIG. 5 shows the batch of pipe being rotated or rolled out of dryer system 10 to galvanizing feeder station 24. Preferably, each pipe is gradually rolled off the top of the batch until the entire batch is transported onto galvanizing feeder station 24. The retention time that the pipe resides in dryer system 10, may vary from one galvanization process to another. For example, the retention time is a function of the dry rate discussed above, and may also be a function of the rate at which the parts can be removed from the molten zinc bath. However, by operating the dryer at a maximum hot air temperature of about 125° C., the dried parts can be held in the dryer for indefinite extended periods of time without degradation or burning of the preflux.

Metal parts having surface temperatures of a maximum of about 125° C. are immersed into the galvanizing tank containing molten zinc. Preferably, each metal part passes through a molten top-flux that floats on the surface of the galvanizing tank, although a top-flux is not necessary to produce continuous, void-free coatings. Top-fluxes are well known in the art. The molten zinc bath contains about 0.1 or less by weight lead, and preferably about 0.05% or less, more preferably about 0.005% or less, and even more preferably about 0.003% or less by weight lead. The molten zinc bath can contain aluminum. Preferably, the molten zinc bath contains between about 0.005% and about 0.015% aluminum or more.

A dryer system used in the inventive process herein can be designed in many possible configurations. The dryer system is preferably designed to house metal parts in a way that maximizes the surface area to be contacted by the flow of dry air, and yet, also minimizes the loss of dry air. For example, FIG. 1 shows tank 12 of dryer system 10, situated adjacent to dry air source 14, and tank 12 has walls that are shaped to funnel dry air along the longitudinal axes of the pipe. Tank 12 is also properly sized to allow movement of the parts during drying. If a divider apparatus is employed, it should be designed such that all of the individual parts of a batch can be rotated enough that they are thoroughly dried and achieve a maximum surface temperature of about 125° C.

Figure 6:
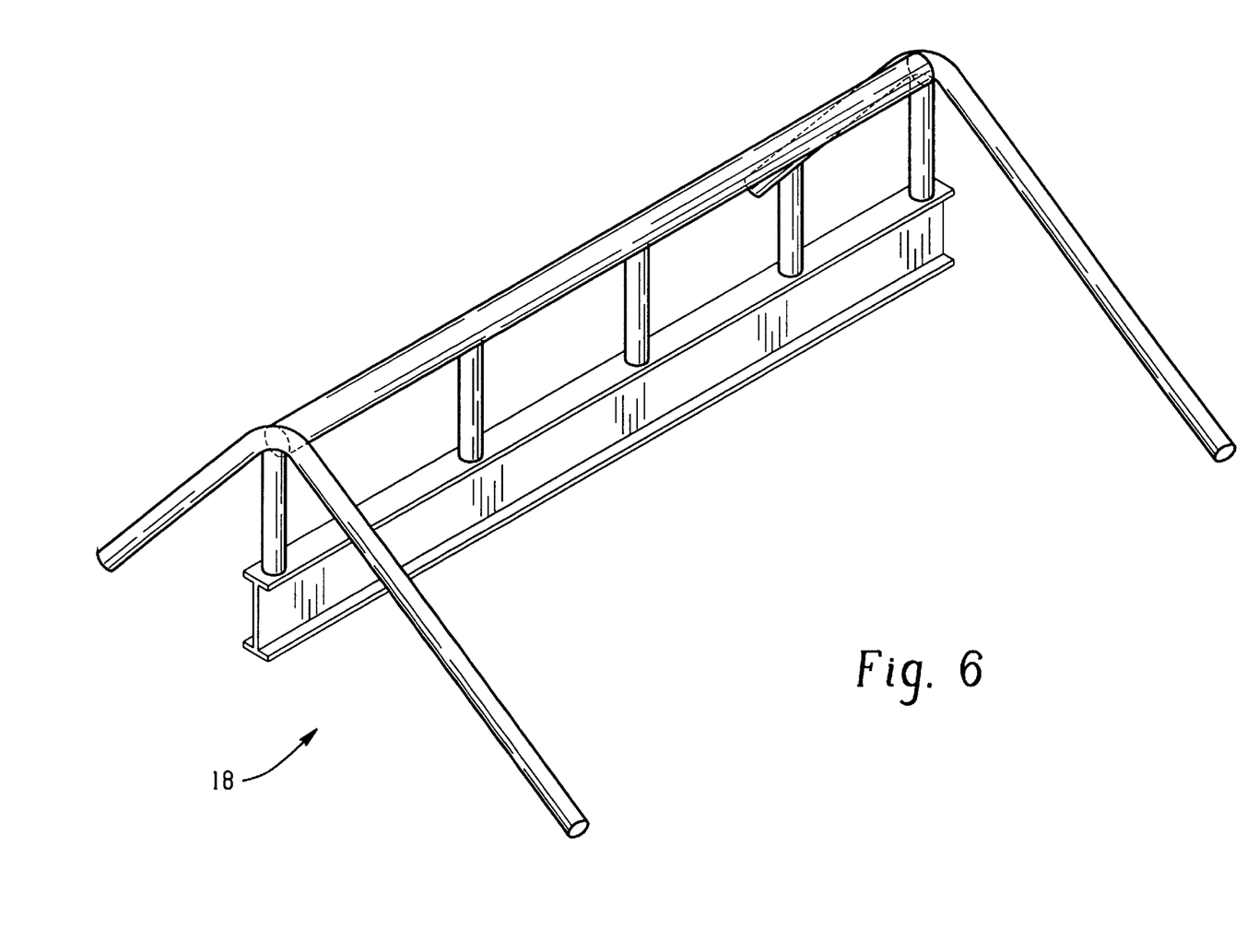
FIG. 6 is a perspective view of the divider apparatus that is utilized to separate and rotate the individual length of pipe.

The configuration of a divider apparatus is dependent upon the geometry of the parts to be galvanized. FIG. 6 shows a perspective view of divider apparatus 18. When the metal parts are pipe, divider apparatus 18 can be triangular shaped so that when a bundle of pipe comes into contact with the top of divider apparatus 18, many of the pipe members are separated or at least caused to rotate or move relative to adjacent pipe members. FIGS. 2 through 5, illustrate the side elevation view of the triangular shaped divider apparatus 18. The of top of the triangle is off-center, the base angles of the triangle are unequal, and thus, the triangle is a scalene triangle. When the top of the triangle is located directly above the midpoint of the base of the triangle, the divider apparatus is less effective in rotating pipe members to expose all surfaces to dry air. In such a case, many of the pipe members can be separated from adjacent pipe members, although, a substantially equal division of the batch can cause several pipe members to remain in the same positions relative to adjacent pipe members, and consequently cause some surfaces to remain wet.

Other modifications and variations of the present invention are possible in light of the above teachings. For example, many modifications of the dryer system may be made. It is to be understood, however, that changes may be made in the particular embodiments described above which are within the full intended scope of the invention as defined in the appended claims.

What is claimed is:

1. A low lead or no-lead galvanization batch process for galvanizing metal parts, the process comprising:
    applying a pre-flux solution having a temperature of at least about 65° C. to the parts;
    drying the parts in a batch while the parts remain in contact with one another such that the surfaces of the parts are essentially dry and the temperature of the parts does not exceed about 125° C.; and
    applying molten zinc to the parts to form a galvanized coating comprising about 0.1% by weight or less lead on the parts.

2. The process of claim 1 wherein the parts are not contacted with a top-flux during the galvanization process.

3. A low lead or no-lead galvanization batch process for galvanizing metal parts, the process comprising:
    applying a pre-flux solution having a temperature of at least about 65° C. to the parts;
    drying the parts in a batch such that the surfaces of the parts are essentially dry and the temperature of the parts does not exceed about 125° C.; and
    applying molten zinc to the parts to form a galvanized coating comprising 0.1% or less by weight lead on the parts;
    wherein the parts are in contact with one another and are rotated with respect to one another as they are dried.

4. The process of claim 3 wherein the galvanized coating comprises about 0.005% or less by weight lead.

5. The process of claim 3 further comprising:
    applying a top-flux to the parts before applying molten zinc to the parts.

6. The process of claim 3 wherein the parts are not contacted by a top-flux during the galvanization process.

7. The process of claim 3 wherein the metal parts comprise pipe members arranged in a batch; and,
    wherein the pipe members contact adjacent pipe members at contact surfaces substantially along the longitudinal surfaces of the pipe members during drying.

8. The process of claim 7 wherein the pipe members are rotated in a radial direction such that substantially all contact surfaces of the pipe members are exposed to air during drying.

9. The process of claim 7 wherein the pipe members are dried in a dryer system and the dryer system comprises a dry air source that comprises steam coils and an air blower that forces air along the surfaces of the pipe members; and,
    wherein the temperature of the air is controlled by regulating the number of steam coils or the steam temperature or both.

10. The process of claim 9 wherein the air from the dry air source does not exceed a temperature of about 125° C.

11. The process of claim 9 wherein air from the dry air source is blown along the longitudinal axis of the pipe until the pipe is essentially thoroughly dry.

12. The process of claim 11 wherein the dryer system further comprises a descrambler system, and wherein the descrambler system transports the batch of pipe and rotates the pipe in a radial direction.

13. The process of claim 12, wherein the dryer system further comprises a divider apparatus; and,
    wherein the descrambler system moves the batch of pipe into contact with the divider apparatus to cause pipe members to rotate about their respective longitudinal axes.

14. The process of claim 13 wherein the descrambler system comprises a chain and a sprocket that rotates to lift and lower the chain to rotate the pipe members.

15. The process of claim 13 wherein contact between the divider apparatus and the batch of pipe causes the pipe members to rotate and become separated from adjacent pipe members.

16. The process of claim 15 wherein the profile shape of the divider apparatus is a scalene triangle.

17. A low lead or no lead galvanization batch process for galvanizing pipe, the process comprising:
    applying a pre-flux solution having a temperature of at least 65° C. to the pipe members;
    drying the pipe members arranged in a batch by rotating the pipe members while in contact with adjacent pipe members as they are dried at a maximum temperature of about 125° C. such that the pipe members are essentially dry; and,
    immersing the pipe members into a molten zinc bath comprising about 0.1% by weight or less lead to form a galvanized coating on the pipe members.

18. The process of claim 17 wherein the molten zinc comprises aluminum.

19. The process of claim 17 wherein the molten zinc comprises between about 0.005% to about 0.015% by weight aluminum.

20. The process of claim 17 wherein the molten zinc comprises about 0.005% by weight or less lead.

21. A process for galvanizing metal parts comprising:
    applying an aqueous pre-flux having a temperature of at least about 65° C. to the parts;
    contacting the parts arranged in a batch with a drying air at elevated temperature without raising the surface temperature of the parts above about 125° C., the parts being moved with respect to one another during air contacting so that essentially all surfaces of the parts are dried; and,
    applying molten zinc to the parts toから a galvanized coating comprising 0.1% or less by weight lead on the parts surface.

22. The process of claim 21 wherein the parts are in contact with one another when dried.

23. A low lead or no-lead galvanization batch process for galvanizing metal parts, the process comprising:
    applying an aqueous pre-flux having a temperature of at least about 65° C. to the parts;
    contacting the parts arranged in a batch with a drying air at elevated temperature without raising the surface temperature of the parts above about 125° C., the parts being moved with respect to one another during air contacting so that essentially all surfaces of the parts are dried; and
    applying molten zinc to the parts to form a galvanized coating comprising 0.1% or less by weight lead on the parts surface;
    wherein the parts are in surface contact with one another during air contacting, and further wherein relative movement of the parts during air contacting causes respective contacting surfaces of the parts to change whereby essentially all surfaces of the parts are dried.

24. The process of claim 23 wherein the parts are rotated with respect to one another.

25. The process of claim 24 wherein the parts are pipe members which are rotated about their respective longitudinal axes during air contacting.

26. A process for galvanizing metal parts comprising:

applying a pre-flux to the parts;

drying the parts without heating the parts above about 125° C.; and, applying molten zinc to the parts to form a galvanized coating containing no more than 0.1% lead wherein at least some parts are in contact with one another along respective contacting surfaces while being dried, and further wherein contacting parts are moved with respect to one another while being dried so that the contacting surfaces thereof can be essentially completely dried before the molten zinc is applied.

27. The process of claim 26, wherein the parts are in contact with one another along a first set of contacting surfaces, and further wherein after the parts are moved with respect to one another they are in contact with one another along a second set of contacting surfaces.

28. The process of claim 26, wherein molten zinc is applied by dipping the parts in a molten zinc bath having a top flux thereon.

29. The process of claim 26, wherein molten zinc is applied by dipping the parts in a molten zinc bath not having a top flux thereon.

* * * * *